United States Patent [19]
Burhop et al.

[11] Patent Number: 5,854,210
[45] Date of Patent: Dec. 29, 1998

[54] USE OF CROSS-LINKED HEMOGLOBIN IN TREATING SUBARACHNOID HEMORRHAGE

[75] Inventors: Kenneth E. Burhop, Mundelein, Ill.; Daniel J. Cole, Redlands, Calif.

[73] Assignee: Baxter International Inc., Deerfield, Ill.

[21] Appl. No.: 747,941

[22] Filed: Nov. 12, 1996

Related U.S. Application Data

[63] Continuation-in-part of Ser. No. 419,209, Apr. 10, 1995, abandoned.

[51] Int. Cl.⁶ ..................................................... A61K 38/16
[52] U.S. Cl. .................................................................. 514/6
[58] Field of Search .................................................... 514/6

[56] References Cited

U.S. PATENT DOCUMENTS

| | | |
|---|---|---|
| Re. 34,271 | 6/1993 | Walder . |
| 2,464,284 | 10/1949 | Alles . |
| 3,238,101 | 3/1966 | Fruhstorfer . |
| 3,681,459 | 8/1972 | Hughes et al. . |
| 3,925,344 | 12/1975 | Mazor . |
| 4,001,401 | 1/1977 | Bonsen et al. . |
| 4,053,590 | 10/1977 | Bonsen et al. . |
| 4,103,687 | 8/1978 | Ishii . |
| 4,529,719 | 7/1985 | Tye . |
| 4,598,064 | 7/1986 | Walder . |
| 4,600,531 | 7/1986 | Walder . |
| 4,757,052 | 7/1988 | Markov . |
| 4,826,811 | 5/1989 | Sehgal et al. . |
| 4,988,515 | 1/1991 | Buckberg . |
| 4,994,444 | 2/1991 | Zikria . |
| 5,049,695 | 9/1991 | Abraham et al. . |
| 5,059,712 | 10/1991 | Griffith . |
| 5,079,337 | 1/1992 | Leonard et al. . |
| 5,110,909 | 5/1992 | Dellacherie et al. . |
| 5,122,539 | 6/1992 | Abraham et al. . |
| 5,128,452 | 7/1992 | Hai et al. . |
| 5,194,590 | 3/1993 | Sehgal et al. . |
| 5,248,766 | 9/1993 | Nelson et al. . |
| 5,248,785 | 9/1993 | Abraham et al. . |
| 5,268,500 | 12/1993 | Lalezari et al. . |
| 5,290,803 | 3/1994 | Abraham et al. . |
| 5,295,944 | 3/1994 | Teicher et al. . |
| 5,334,706 | 8/1994 | Wong . |
| 5,370,870 | 12/1994 | Abraham et al. . |
| 5,382,680 | 1/1995 | Nho et al. . |
| 5,386,014 | 1/1995 | Nho et al. . |
| 5,428,007 | 6/1995 | Fischer et al. . |
| 5,432,191 | 7/1995 | Abraham et al. . |
| 5,434,168 | 7/1995 | Stokbroekx et al. . |
| 5,439,882 | 8/1995 | Feola et al. . |
| 5,449,759 | 9/1995 | Hoffman et al. . |
| 5,464,814 | 11/1995 | Sehgal et al. . |
| 5,478,806 | 12/1995 | Nho . |
| 5,498,421 | 3/1996 | Grinstaff et al. . |
| 5,510,464 | 4/1996 | Przybelski . |
| 5,591,710 | 1/1997 | Hsia . |

FOREIGN PATENT DOCUMENTS

| | | |
|---|---|---|
| 660257 | 9/1993 | Australia . |
| 2087504 | 7/1993 | Canada . |
| 0140640 | 5/1985 | European Pat. Off. . |
| 0143832 | 2/1989 | European Pat. Off. . |
| 0361719 | 9/1989 | European Pat. Off. . |
| 0361720 | 4/1990 | European Pat. Off. . |
| 0431129 | 6/1991 | European Pat. Off. . |
| 0446699 | 9/1991 | European Pat. Off. . |
| 0584876 | 3/1994 | European Pat. Off. . |
| 63208523 | 8/1988 | Japan . |
| 7404140 | 10/1974 | Netherlands . |
| 8404248 | 11/1984 | WIPO . |
| 8707832 | 12/1987 | WIPO . |
| 9109615 | 7/1991 | WIPO . |
| 9213875 | 8/1992 | WIPO . |
| 9220368 | 11/1992 | WIPO . |
| 9220369 | 11/1992 | WIPO . |
| 9316720 | 9/1993 | WIPO . |
| WO 93/16721 | 9/1993 | WIPO . |
| 9422482 | 10/1994 | WIPO . |
| 9525121 | 3/1995 | WIPO . |
| 9629346 | 9/1996 | WIPO . |

OTHER PUBLICATIONS

The Blood Sustitutes: Markets, Products and Red Cell Sourcing. The Marketing Research Bureau, Inc., pp. 182–186, 1994.

Asano et al., Endothelin: A Potential Modulator of Cerebral Vasospasm. European Journal of Pharmacology, vol. 190, pp. 365–372, 1990.

Asano et al., Endothelin and the Production of Cerebral Vasospasm in Dogs. Biochemical and Biophysical Research Communications, vol. 159, No. 3, pp. 1345–1351, 1989.

Barve et al., Dose–Dependent Effect of Diaspirin Crosslinked Hemoglobin on the Systemic and Regional Blood Circulation in Rats. Art. Cells, Blood Subs., and Immob. Biotech., vol. 24, No. 4, p. 306, 1996 (abstract).

Bilello et al., Diaspirin Cross Linked Hemoglobin (DCLHb): Control of Pressor Effect with Anti–Hypertensive Agents. ISBS 1993 Program and Abstracts, (1 page).

Bilello et al., Diaspirin Crosslinked Hemoglobin (DCLHb): Control of Pressor Effect with Anti–Hypertensive Agents. Art. Cells, Blood Subs., and Immob. Biotech., vol. 22, No. 3, pp. 819–825, 1994.

Biro et al. The Effect of Hemodilution with Stroma–Free Hemoglobin and Dextran on Collateral Perfusion of Ischemic Myocardium in the Dog. American Heart Journal, vol. 99, No. 1, pp. 64–75, 1980.

Bowes et al. Diaspirin Cross–Linked Hemogolbin Improves Neurological Outcome Following Reversible but Not Irreversible CNS Ischemia in Rabbits. Chemical Abstracts, vol. 122, No. 13, Abstract No. 151066q, pp. 45–46, 1995.

(List continued on next page.)

Primary Examiner—Raymond Henlev, III
Attorney, Agent, or Firm—Senniger, Powers, Leavitt & Roedel

[57] ABSTRACT

A hemoglobin preparation is administered following subarachnoid hemorrhage to dramatically reduce the tissue area of hypoperfusion and the extent of neuronal damage in the area of hypoperfusion.

42 Claims, 2 Drawing Sheets

OTHER PUBLICATIONS

Bowes et al. Diaspirin Cross–linked Hemoglobin Improves Neurological Outcome Following Reversible But Not Irreversible CNS Ischemia in Rabbits. Department of Medicinal Chemistry, Virginia Commonwealth University, pp. 2253–2257, 1994.

Bowes et al. Hemodilution with Diaspirin Cross–Linked Hemoglobin (DCLHb) Reduces Neurological Damage Following Reversible But Not Irreversible CNS Ischemia in Rabbits. Soc. Neurosci., vol. 19, Abstract No. 673.8, p. 1643, 1993.

Bowman et al. Actions on the Cardiovascular System of an Inhibitory Material Extracted From the Bovine Retractor Penis. Br. J. Pharmac., vol. 72, pp. 365–372, 1981.

Buga et al. Endothelium–Derived Nitric Oxide Relaxes Nonvascular Smooth Muscle. European Journal of Pharmacology, vol. 161, pp. 61–71, 1989.

Burhop et al. Diaspirin Crosslinked Hemoglobin (DCLHb): Application in the Treatment of Hypovolemic Hemorrhagic Shock. Intl. J. Crit. Care Med., vol. 5, No. 2 Supplement, Abstract No. 19, 1994.

Byrne et al. Investigation of the Vasoconstrictor Action of Subarachnoid Haemoglobin in the Pig Cerebral Circulation in Vivo. Br. J. Pharmacol., vol. 97, pp. 669–674, 1989.

Chappell et al. Hemodilution with Diaspirin Cross–linked Hemoglobin Lowers Intracranial Pressure, Improves Cerebral Perfusion Pressure and Reduces Fluid Requirement Following Head Injury and Shock. Surgical Forum, vol. 46, No. 0, pp. 469–471, 1995.

Cheung et al. Preliminary Characterization of Vasocontractile Activities in Erythrocytes. Journal of Neurosurgery, vol. 53, pp. 37–43, 1980.

Chyatte et al. Cerebral Vasospasm: Evidence Supporting an Inflammatory Etiology. Cerebral Vasospasm, pp. 357–365, 1988.

Clower et al. Endothelial Injury following Experimental Subarachnoid Hemorrhage in Rats: Effects on Brain Blood Flow. The Anatomical Record, vol. 240, pp. 104–114, 1994.

Cocks et al. Oxyhaemoglobin Increases the Production of Endothelin–1 by Endothelial Cells in Culture. European Journal of Pharmacology, vol. 196, pp. 177–182, 1991.

Coetzee et al. Halothane and the Reperfusion Injury in the Intact Animal Model. Anesth. Analg., vol. 76, No. 4, pp. 734–744, 1993.

Cole et al. Hypervolemic–Hemodilution and Hypertension During Temporary Middle Cerebral Artery Occlusion in Rats: The Effect on Blood–Brain Barrier Permeability. The Canadian Journal of Neurological Sciences, vol. 17, No. 4, pp. 372–377, 1990.

Cole et al. Effects of Viscosity and Oxygen Content on Cerebral Blood Flow in Ischemic and Normal Rat Brain. Journal of the Neurological Sciences, vol. 124, pp. 15–20, 1994.

Cole et al. Focal Cerebral Ischemia in Rats: Effect of Oncotic Pressure of a Molecular Hemoglobin Preparation on Infarct Volume in Rats. Anesth. Analog, vol. 80, No. S82, 1995

Cole et al. Effects of Oncotic Pressure of a Molecular Hemoglobin Solution on Focal Cerebral Ischemia in Rats. Anesthesia and Analgesia, vol. 83, No. 2, pp. 342–347, 1992.

Cole et al. Hemodilution and Hypertension Effects on Cerebral Hemorrhage in Cerebral Ischemia in Rats. Stroke, vol. 21, No. 9, pp. 1333–1339, 1990.

Cole et al. The Effect of Molecular Hemoglobin's Nitric Oxide Binding Properties on Cerebral Ischemic Injury in Rats. Anesth. Analog, vol. 80, No. S83, 1995.

Cole et al. Diaspirin Crosslinked Hemoglobin (DCLHb): Effect of Hemodilution During Focal Cerebral Ischemia In Rats. ISBS 1993 Program and Abstracts, (1 page).

Cole et al. Diaspirin Crosslinked Hemoglobin (DCLHb): Effect of Hemodilution During Focal Cerebral Ischemia in Rats. Art. Cells, Blood Subs., and Immob. Biotech., vol. 22, No. 3, pp. 813–818, 1994.

Cole et al. Hemodilution During Cerebral Ischemia in Rats: Effects of Stroma–Free Hemoglobin on Brain Injury. Anesth. Analog, vol. 74, Abstract S50, 1992.

Cole et al. Focal Cerebral Ischemia in Rats: Effect of Hypervolemic Hemodilution with Diaspirin Cross–Linked Hemoglobin Versus Albumin on Brain Injury and Edema. Anesthesiology, vol. 78, No. 2, pp. 335–342, 1993.

Cole et al. Focal Cerebral Ischemia in Rats: Effect of Hemodilution with x—x Cross–Linked Hemoglobin on Brain Injury and Edema. The Canadian Journal of Neurological Sciences, vol. 20, No. 1, pp. 30–36, 1993.

Cole et al. Focal Cerebral Ischemia in Rats: Effect of Hemodilution with x—x Cross–Linked Hemoglobin on CBF. Journal of Cerebral Blood Flow & Metabolism, vol. 12, No. 6, pp. 971–976, 1992.

Cole et al. Control of Cross–linked Hemoglobin's (Hb) Pressor Response. Circ. Shock, vol. 80, No. 10, p. 221a, 1992 (abstract).

Cosentino et al. Does Endothelin–1 Play a Role in the Pathogenesis of Cerebral Vasospasm? Stroke, vol. 25, No. 4, pp. 904–908, 1994.

Deby–Dupont et al. Hemoglobin–based Red Cell Substitutes: Preliminary Human Studies. Yearbook of Intensive Care and Emerg. Med., pp. 264–275, 1994.

Delgado et al. Subarachnoid Haemorrhage in the Rat: Angiography and Flourescence Microscopy of the Major Cerebral Arteries. Stroke, vol. 16, No. 4, pp. 595–601.

Edvinsson et al. Neuropeptide Y and Vasoactive Intestinal Peptide in experimental Subarachnoid Hemorrhage: Immunocytochemistry, Radioimmunoassy and Pharmacology. Acta Neurol. Scand., vol. 83, pp. 103–109, 1991.

Elger et al. Magnetic Resonance Imaging Study on the Effect of Levemopamil on the Size of Intracerebral Hemorrhage in Rats. Stroke, vol. 25, No. 9, pp. 1836–1841, 1994.

Estep. Efficacy and Safety of a Diaspirin Modified Hemoglobin Solution. ISBT Presentation, 1988.

Estep et al. Diaspirin Crosslinked Hemoglobin (DCLHb): A Review of Cardiovascular and Pharmacologic Properties. ISBS 1993 Program and Abstracts, (1 page).

Estep et al. The Purification of Hemoglobin Solution by Heating. The Red Cell: Seventh Ann Arbor Conference, pp. 325–338, 1989.

Farmer et al. Preclinical Data and Clinical Trials with Diaspirin Cross–linked Hemoglobin. Artif. Red Cells, pp. 177–185, 1995.

Feola et al. Improved Oxygenation of Ischemic Myocardium by Hemodilution with Stroma–Free Hemoglobin Solution. Chest, vol. 75, No. 3, pp. 369–375, 1979.

Foley et al. Cytotoxic Effects of Bloody Cerebrospinal Fluid on Cerebral Endothelial Cells in Culture. Journal of Neurosurgery, vol. 81, pp. 87–92, 1994.

Fratantoni, Points to Consider in the Safety Evaluation of Hemoglobin–Based Oxygen Carriers. Transfusion, vol. 31, No. 4, pp. 369–371, 1991.

Freas et al. Effect of Diaspirin Cross–Linked Hemoglobin Solution on Isolated Porcine Pulmonary Artery and Vein Rings. FASEB J., vol. 7, No. 3, Part 1, Abstract No. 1820, p. A314, 1993.

Freas et al. Contraction of Isolated Procine Blood Vessels by Diaspirin Cross Linked Hemoglobin. Anesth., vol. 79, No. 3A, Abstract No. 667, 1993.

Freas et al. Diaspirin Cross Linked Hemoglobin (DCLHb): Action on Isolated Porcine Pulmonary Blood Vessels. ISBS Presentation 1993 (1 page).

Fujii et al. Experimental Vasospasm in Cultured Arterial Smooth–Muscle Cells. Part I: Contractile and Ultrastructural Changes Caused By Oxyhemoglobin. Cerebral Vasospasm, pp. 87–96, 1988.

Fujii et al. Experimental Vasospasm in Cultured Arterial Smooth–Muscle Cells. Part I: Contractile and Ultrastructural Changes Caused By Oxyhemoglobin. Journal of Neurosurgery, vol. 69, pp. 92–97, 1988.

Gaetani et al. Experimental Subarachnoid Hemorrhage: Events Related to Anti–Oxidant Enzymatic Systems and Eicosanoid Peroxide Enhancement. Neurochemical Reseach, vol. 19, No. 7, pp. 839–844, 1994.

Gaetani et al. Effect of High–Dose Methylprednisolone and U74006F on Eicosanoid Synthesis After Subarachnoid Hemorrhage in Rats. Stroke, vol. 22, No. 2, pp. 215–220, 1991.

Germano et al. Blood–Brain Barrier Permeability Changes After Experimental Subarachnoid Hemorrhage. Neurosurgery, vol. 30, No. 6, pp. 882–886, 1992.

Gillespie et al. A Comparison of Haemoglobin and Erythrocytes as Inhibitors of Smooth Muscle Relaxation by the NANC Transmitter in the BRP and Rat Anococcygeus and by EDRF in the Rabbit Aortic Strip. Br. J. Pharmacol., vol. 98, No. 2, pp. 445–450, 1989.

Grotta. A Glimpse to the Future: Multitherapy Trials. Cerebrovasc. Dis., vol. 5, Suppl. 1, pp. 27–30, 1995.

Grotta et al. DCLH for Focal Ischemia and Reperfusion. Stroke, vol. 26, No. 1, p. 47, 1995 (abstract).

Grotta et al. Hypervolemic Hemodilution Treatment of Acute Stroke–Results of a Randomized Multicenter Trial Using Pentastarch. Stroke, vol. 20, No. 3, pp. 317–323, 1989.

Gulati et al. Diaspirin Cross–Linked Hemoglobin (DCLHb): Involvement of Adrenergic Mechanisms in the Pressor Effect. Art. Cells, Blood Subs., and Immob. Biotech., vol. 22, No. 3, pp. 603–612, 1994.

Gulati et al. Diaspirin Crosslinked Hemoglobin (DCLHb): Involvement of Adrenergic Mechanisms in the Pressor Effect. ISBS 1993 Program and Abstracts, (1 page).

Gulati et al. Role of Adrenergic Mechanisms in the Pressor Effect of Diaspirin Cross–Linked Hemoglobin. J. Lab. Clin. Med., vol. 124, No. 1, pp. 125–133, 1994.

Gulati et al. Prazosin Blocks the Pressor But Not the Regional Circulatory Efects of Diaspirin Crosslinnked Hemoglobin. Life Sciences, vol. 55, No. 2, pp. 121–130, 1994.

Gulati et al. Cardiovascular Effects of Unmodified Stroma- –Free (SFHb) and Diaspirin Crosslinked (DCLHb) Hemoglobin. Canad. J. Physiol. Pharmacology; X11th International Congress of Pharmacology, 1994 (Abstract No. P1.12.8).

Gulati et al. Effect of Stroma–Free Hemoglobin and Diaspirin Cross–Linked Hemoglobin on the Regional Circulation and Systemic Hemodynamics. Life Sciences, vol. 55, No. 10, pp. 827–837, 1994.

Gulati et al. Effect of BQ–123, an Endothelin Receptor Antogonist, on Regional Circulatory Effects of Diaspirin Crosslinked Hemoglobin. Canad. J. Physiol. Pharmacology; X11th International Congress of Pharmacology, 1994 (Abstract No. P1.14.49).

Gulati et al. Regional Circulatory Effects of Diaspirin Crosslinked Hemoglobin Can Be Blocked by the Endotheline (ET) Antagonist, BQ–123. FASEB J., vol. 8, No. 5, Abstract No. 3624, p. A625, 1994.

Haley. Principles of Pharmaceutical Therapy for Vasospasm Following Subarachnoid Hemorrhage. Principles of Pharmaceutical Therapy for Vasospasm, pp. 85–89, 1992.

Handa et al. Time Course of the Impairment of Cerebral Autoregulation During Chronic Cerebral Vasospasm After Subarachnoid Hemorrhage in Primates. J. Neurosurg., vol. 76, pp. 493–501, 1992.

Hariman et al. Regional Changes in Blood Flow, Extracellular Potassium and Conduction During Myocardial Ischemia and Reperfusion. JACC, vol. 21, No. 1, pp. 798–808, 1993.

Hart et al. Diaspirin Cross–Linked Hemoglobin (DCLHb) Effects on Isolated Blood Vessels. FASEB J., vol. 9, No. 3, Abstract No. 1878, p. A324, 1995.

Hauck et al. Intracoronary Diaspirin Crosslinked Hemoglobin (DCLHb) Infusion During Coronary Balloon Occlusion in Dogs and Pigs. Biomaterials, Artificial Cells, and Immobilization Biotechnology, vol. 19, No. 2, p. 393, 1991 (abstract).

Hongo et al. Intravascular Vasodilator Agents Reverse Experimental Vasospasm. Cerebral Vasospasm, pp. 443–447, 1988.

Itoh et al. Prevention of Delayed Vasospasm by an Endothelin ETA Receptor Antagonist, BQ–123: Change of ETA Receptor mRNA Expression in a Canine Subarachnoid Hemorrhage Model. Journal of Neurosurgery, vol. 81, pp. 759–764, 1994.

Iyer et al. Endothelin Concentration in the Central Nervous and Cardiovascular Systems During Development of Hypertensive Rats. FASEB J., Abstracts Part I, vol. 8, No. 4, Abstract No. 442, 1994.

Jakobsen, Brain Ischemia In Subarachnoid Hemorrhage. Anesthesia Service, Virginia Medical Center, pp. 3–32, 1992.

Jan et al. Coronary Hemodynamics and Oxygen Utilization After Hematocrit Variations in Hemorrhage. Am. J. Physiol., vol. 239, pp. H326–H332, 1980.

Jennings et al. Reperfusion Injury, Definitions and Historical Background. Myocardial Protection: the Pathophysiology of Reperfusion and Reperfusion Injury, pp. 1–11, 1992.

Jeroudi et al. Myocardial Reperfusion Injury: Role of Oxygen Radicals and Potential Therapy with Antioxidants. The American Journal of Cardiology, vol. 73, pp. 2B–7B, 1994.

Jing et al. Effects of Halothane and Isoflurane on Diaspirin Crosslinked Hemoglobin–Induced Contractions of Porcine Pulmonary Veins. Art. Cells, Blood Subs., and Immob. Biotech., vol. 22, No. 5, Abstract No. A107, 1994.

Jing et al. Effects of Halogenated and Non–Halogenated Anesthetics on Diaspirin Crosslinked Hemoglobin Induced Contractions of Porcine Pulmonary Veins. Artif. Cells, Blood Substitutes, Immobilization Biotechnol., vol. 23, No. 4, pp. 487–494, 1995.

Kasuya et al. Mechanism of Oxyhemoglobin–Induced Release of Endothelin–1 From Cultured Vascular Endothelial Cells and Smooth–Muscle Cells. J. Neurosurg., vol. 79, pp. 892–898, 1993.

Katsuyama et al. Nitric Oxide Mediates the Hypertensive Resonse to a Modified Hemoglobin Solution (DCLHb) in Rats. Art. Cells, Blood Subs., and Immob. Biotech., vol. 22, No. 1, pp. 1–7, 1994.

Kawakami et al. Suppression of the Cerebral Vasospastic Actions of Oxyhemoglobin by Ascorbic Acid. Neurosurgery, vol. 28, No. 1, pp. 33–40, 1991.

Kelm et al. Control of Coronary Vascular Tone by Nitric Oxide. Circulation Research, vol. 66, No. 6, pp. 1561–1575, 1990.

Kim et al. Effects of Hemoglobin Perfusion of Contractile Function of the Isolated Ventricular Septa. Biomat. Art. Cells, Art. Org., vol. 16, Nos. 1–3, 331–345, 1988.

Kim et al. Effects of Hemoglobin Perfusion on Contractile Function of the Isolated Ventricular Septa. Chemical Abstracts, vol. 109, No. 21, Abstract No. 183274d, p. 38, 1988.

Kline et al. Diaspirin Crosslinked Hemoglobin (DCLHb): Efficacy in Treatment of Focal Cerebral Ischemia. ISBS 1993 Program and Abstracts, (1 page).

Kloner, Does Reperfusion Injury Exist in Humans? J. Am. Coll. Cardiol., vol. 21, No. 2, pp. 537–545, 1993.

Konishi et al. Treatment of Cerebral Vasospasm with Dilation Balloon Catheter: Basic Study of Percutaneous Transluminal Angioplasty. Cerebral Vasospasm, pp. 509–511, 1988.

Kubota et al. The Kinetics of Lymphocyte Subsets and Macrophages in Subarachnoid Space After Subarachnoid Hemorrhage in Rats. Stroke, vol. 24, No. 12, pp. 1993–2001, 1993.

Levin et al. Complications During Hemodialysis. Citation Unknown, pp. 172–197.

Lie, The Reasons Why Clinical Cardiologists Disregard Reperfusion Arrhythmias. Cardiovascular Research, vol. 27, p. 1906, 1993.

Linz et al. Diaspirin Crosslinked Hemoglobin Infusion Reduces Infarct Size During Coronary Ischemia/Reperfusion in Swine. FASEB J., vol. 9, No. 3, Abstract No. 54, p. A9, 1995.

Liu et al. Reduction of Postischaemic Ventricular Dysfunction and Arrhythmias by Trapping Hydroxyl Radicals with Salicylic Acid. Int. J. Tiss. Reac., vol. 15, No. 1, pp. 25–30, 1993.

Ljunggren et al. History and Epidemiology of SAH and Cerebrovascular Malformations. History and Epidemiology of SAH, pp. 3–12.

Macdonald et al. A Review of Hemoglobin and the Pathogenesis of Cerebral Vasospasm. Stroke, vol. 22, No. 8, pp. 971–982, 1991.

Macdonald et al. Cerebral Vasospasm and Free Radicals. Free Radical Biology & Medicine, vol. 16, No. 5, pp. 633–643, 1994.

Macdonald et al. New Evidence Pointing to Oxyhemoglobin as the Cause of Vasospasm. Neurosurgery Section, University of Chicago Medical Center, pp. 27–31, 1994.

Malcolm et al. Diaspirin Cross Linked Hemoglobin (DCLHb): Characterization of Hemodynamic Response in Rats. ISBS 1993 Program and Abstracts, (1 page).

Malcolm et al. Characterization of the Hemodynamic Response to Intravenous Diaspirin Crosslinked Hemoglobin Solution in Rats. Art. Cells, Blood Subs., and Immob. Biotech., vol. 22, No. 1, pp. 91–107, 1994.

Marks, Hemoglobin Solution Effects on the Heart. Letterman Army Institute of Research, Report No. 219, 1986.

Martin et al. Selective Blockade of Endothelium–Dependent and Glyceryl Trinitrate–Induced Relaxation by Hemoglobin and by Methylene Blue in the Rabbit Aorta. The Journal of Pharmacology and Experimental Therapeutics, vol. 232, No. 3, pp. 708–716, 1985.

Marzatico et al. Effects of Nicardipine Treatment on NA+–K+ ATPase and Lipid Peroxidation After Experimental Subarachnoid Haemorrhage. Acta Neurochir, vol. 108, pp. 128–133, 1991.

Mayberg et al. The Role of Hemoglobin in Arterial Narrowing After Subarachnoid Hemorrhage. J. Neurosurg., vol. 72, pp. 634–640, 1990.

McIlhany et al. In vivo Characterization of Vasocontractile Activities in Erythrocytes. J. Neurosurg., vol. 58, pp. 356–361, 1983.

McKenzie et al. Effects of Diaspirin Crosslinked Hemoglobin During Coronary Angioplasty in the Swine. Cardiovascular Research, Vo. 28, pp. 1188–1192, 1994.

McKenzie et al. Effects of Diaspirin Cross–linked Hemoglobin (DCLHb) on Cardiac Function and ECG in the Swine. Biomater. Artif. Cells Immob. Biotech., vol. 20, Nos. 2–4, pp. 683–687, 1992.

McKenzie et al. Effects of Diaspirin Cross–linked Hemoglobin (DCLHb) on Cardiac Function and ECG in the Swine. FASEB Journal, vol. 5, No. 5, Abstract No. 1897, 1991.

McKenzie et al. Effects of Intracoronary Infusion of Diaspirin Cross–Linked Hemoglobin (DCLHb) on Cardiac Function and ECG in the Swine. Biomat., Art. Cells & Immob. Biotech., vol. 19, No. 2, (1 page), 1991 (abstract).

Messmer et al. Present State of Intentional Hemodilution. Eur. Surg. Res., vol. 18, pp. 254–263, 1986.

Miao et al. Effects of Bilirubin on Cerebral Arterial Tone in Vitro. Journal of Cerebral Blood Flow and Matabolism, vol. 9, pp. 666–674, 1989.

Muizelaar et al. Effect of Hematocrit Variations on Cerebral Blood Flow and Basilar Artery Diameter in vivo. The American Physiological Society, pp. H949–H954, 1992.

Nagatani et al. The Effect of Hemoglobin and its Metabolites on Energy Metabolism in Cultured Cerebrovascular Smooth–Muscle Cells. J. Neurosurg., vol. 82, pp. 244–249, 1995.

Nanavaty et al. Diaspirin Cross–Linked Hemoglobin (DCLHb): Characterization of Blood Pressure Response in the Swine. ISBS 1993 Program and Abstracts, (1 page).

Naveri et al. Angiotensin IV Reverses the Acute Cerebral Blood Flow Reduction After Experimental Subarachnoid Hemorrhage in the Rat. Journal of Cerebral Blood Flow and Metabolism, vol. 14, pp. 1096–1099, 1994.

Nazer et al. Subarachnoid Hemorrhage Causes Adherence of White Blood Cells to the Cerebral Arterial Luminal Surface. Cerebral Vasospasm, pp. 343–356, 1988.

Nelson et al. Diaspirin Cross–Linked Hemoglobin: An Investigational Drug Exemploifying Hemoglobin–Based Blood Substitutes. Presented at The American Society of Hospital Pharmacists, (6 pages), 1992 (Abstract).

Nolte et al. Diaspirin Crosslinked Hemoglobin: Evaluation of Effects on the Microcirculation of Striated Muscle. Art. Cells, Blood Subs., and Immob. Biotech., vol. 22, No. 3, pp. 587–592, 1994.

Ohlstein et al. Oxyhemoglobin Stimulation of Endothelin Production in Cultured Endothelial Cells. J. Neurosurg., vol. 77, pp. 274–278, 1992.

Okamoto et al. Responses of Fresh Human, Monkey, and Canine Cerebral Arteries to a Red Blood Cell Hemolysate. Cerebral Vasospasm, pp. 311–316, 1988.

Okwuasaba et al. Changes in Vasoactive Properties of Blood Products with Time and Attempted Identification of the Spasmogens. Stroke, vol. 12, No. 6, pp. 775–780, 1981.

Origitano et al. Sustained Increased Cerebral Blood Flow with Prophylactic Hypertensive Hypervolemic Hemodilution ("Triple–H" Therapy) after Subarachnoid Hemorrhage. Neurosurgery, vol. 27, No. 5, pp. 729–740, 1990.

Osaka, Prolonged Vasospasm Produced by the Breakdown Products of Erythrocytes. J. Neurosurg., vol. 47, pp. 403–411, 1977.

Otani et al. Reperfusion Injury Induced by Augmented Oxygen Uptake in the Initial Reperfusion Period Possible Efficacy of Extreme Hemodilution. J. Mol. Cell. Cardiol., vol. 17, No. 5, pp. 457–466, 1985 (abstract only).

Ozaki et al. Possible Role of the Erythrocyte in Causing Prolonged Cerebral Vasospasm. J. Neurosurg., vol. 51, pp. 773–778, 1979.

Peterson et al. The Role of Inflammation in Experimental Cerebral Vasospasm. J. Neurosurgery, vol. 72, pp. 767–774, 1990.

Peterson et al. Evidence of the Role of Hemolysis in Experimental Cerebral Vasospasm. J. Neurosurgery, vol. 72, pp. 775–781, 1990.

Pohl et al. Endothelium–Dependent Modulation of Vascular Tone and Platelet Function. European Heart Journal, vol. 11, Supplement B, pp. 35–42, 1990.

Pohl et al. EDRF–Mediated Shear–Induced Dilation Opposes Myogenic Vasoconstriction in Small Rabbit Arteries. American Journal of Physiology, vol. 261, pp. H2016–H2023, 1991.

Przybelski et al. The Pressor/Perfusion Effect of Diaspirin Cross–Linked Hemoglobin (DCLHb). Yearbook of Intensive and Emerg. Care Med., pp. 252–263, 1994.

Przybelski et al. Diaspirin Cross–Linked Hemoglobin (DCLHb): Phase I Clinical Safety Assessment in Normal Healthy Volunteers. Crit. Care Med., vol. 22, No. 1, Abstract No. A231, (1 page), 1994.

Przybelski et al. Diaspirin Cross–Linked Hemoglobin (DCLHb): Phase I Clinical Safety Assessment in Normal Healthy Volunteers. ISBS 1993 Program and Abstracts (1 page).

Przybelski et al. Diaspirin Cross–linked Hemoglobin (DCLHb): Phase I Clinical Safety Assessment in Normal Healthy Volunteers. WCEDM 1993 Programs and Abstracts, Emergency Medicine, No. 181 (1 page).

Ram et al. Vasospasm Due to Massive Subarachnoid Haemorrhage–a Rat Model. Acta Neurochir (Wien), vol. 110, pp. 181–184, 1991.

Rebello et al. Diaspirin Crosslinked Hemoglobin Reverses the Reduction in Cerebral Blood Flow Induced by Central Endothelin (ET). The FASEB Journal, vol. 8, No. 4, Part II, Abstract No. 4802, pp. A828, 1994.

Rebello et al. Effect of Diaspirin Crosslinked Hemoglobin on the Reduction in Cerebral Blood Flow Induced by Endothelin (ET). Canad. J. Physiol. Pharmacology; X11th International Congress on Pharmacology, 1994 (Abstract No. P13.20.17).

Rebello et al. Effect of Diaspirin a—a Cross Linked Hemoglobin Solution (DCLHb) on Systemic Hemodynamics and Regional Circulation in Rats. FASEB J., vol. 7, No. 4, Part 2, Abstract No. 4328, p. A750, 1993.

Rieder, Hemoglobin Stability: Observations on the Denaturation of Normal and Abnormal Hemoglobins by Oxidant Dyes, Heat and Alkali. The Journal of Clinical Investigation, vol. 49, pp. 2369–2376, 1970.

Roy et al. Systemic Hemodynamics and Regional Circulatory Effects of Centrally Administered Endothelin (ET). FASEB Journal, vol. 8, No. 4, Abstract 1926, pp. A333, 1994.

Sasaki et al. Recent Advances in Research of Cerebral Vasospasm–Possible Participation of Endothelin in the Genesis of Vasospasm. Department of Neurosurgery, University of Tokyo, pp. 32–37, 1994.

Schell et al. Hemodilution During Cerebral Ischemia in Rats: Effects of Stroma–Free Hemoglobin on Blood Flow. Anesth Analog, vol. 74, Abstract S262, 1992.

Schell et al. Hemodilution with Diaspirin Hemoglobin During Cerebral Ischemia in Rats: The Effect on Cerebral Blood Flow. Abstracts–19 Annual Fall Meeting, p. 197, 1989.

Schultz et al. Diaspirin Cross Linked Hemoglobin (DCLHb): Comparison to Various Resuscitative Fluids on Restoration of Base Deficit Following Resuscitation from Hemorrhage in Rats. ISBS 1993 Program and Abstracts, (1 page).

Schultz et al. Diaspirin Cross–Linked Hemoglobin's Pressor Effect is Mediated in Part by Endothelin Release and the Inhibition of Nitric Oxide. Presented at The Society of University Surgeons Resident's Program, 1992 (abstract).

Schultz et al. A Role for Endothelin and Nitric Oxide in the Pressor Response to Diaspirin Cross–linked Hemoglobin. J. Lab. Clin. Med., vol. 122, pp. 301–308, 1993.

Schultz et al. Diaspirin Cross Linked Hemoglobin (DCLHb): Elevation of Mean Arterial Pressure is Mediated Through Endothelin and Nitric Oxide in Rats. Vth International Symposium on Blood Substitutes, 1993 Program and Abstracts, Abstract No. H44.

Seifert et al. Endothelin Concentrations in Patients with Aneurysmal Subarachnoid Hemorrhage. Journal of Neurosurgery, vol. 82, pp. 55–62, 1995.

Sharma et al. Effect of Diaspirin Cross–linked Hemoglobin and Norepinephrine on Systemic Hemodynamics and Regional Circulation in Rats. J. Lab. Clin. Med., vol. 123, No. 2, pp. 299–308, 1994.

Sharma et al. Influence of L–Arginine on Cardiovascular Effects of Diaspirin Crosslinked (DCLHb) and Stroma–Free Hemoglobin (SFHb). Canad. J. Physiol. Pharmacology, X11th International Congress of Pharmacology, 1994 (Abstract No. P14.1.7).

Sharma et al. Yohimbine Modulates Diaspirin Crosslinked Hemoglobin–Induced Systemic Hemodynamics and Regional Circulatory Effects. Critical Care Medicine, vol. 23, No. 5, pp. 874–884, 1995.

Sharma et al. Regional Circulatory and Systemic Hemodynamic Effects of Diaspirin Cross–Linked Hemoglobin in the Rat. Art. Cells, Blood Subs., and Immob. Biotech., vol. 22, No. 3, pp. 593–602, 1994.

Sharma et al. Regional Circulatory and Systemic Hemodynamic Effects of Diaspirin Crosslinked Hemoglobin in the Rat. ISBS 1993 Program and Abstracts, (1 page).

Sharma et al. Cardiovascular Effects of Diaspirin Crosslinked Hemoglboin are Partially Mediated Through A Nitric Oxide (NO) Mechanism. FASEB J., vol. 9, No. 4, Abstract No. 5441, p. A937, 1995.

Sharma et al. Role of NO Mechanism in Cardiovascular Effects of Diaspirin Cross–Linked Hemoglobin in Anesthetized Rats. The American Physiological Society, pp. H1379–H1388, 1995.

Siesjo, Pathophysiology and Treatment of Focal Cerebral Ischemia. Part I: Pathophysiology. Journal of Neurosuregery, vol. 77, pp. 169–184, 1992.

Siesjo, Pathophysiology and Treatment of Focal Cerebral Ischemia. Part II: Mechanisms of Damage and Treatment. Journal of Neurosuregery, vol. 77, pp. 337–354, 1992.

Singh et al. Effect of the Endothelin Converting Enzyme Inhibitor, Phosphoramidon, on Diaspirin Crosslinked Hemoglobin Induced Systemic Hemodynamic and Regional Circulatory Effects in Rats. FASEB J., vol. 9, No. 4, Abstract No. 5439, p. A937, 1995.

Singh et al. Effect of Diaspirin Crosslinked and Stroma–Reduced Hemoglobin on Endothelin–1 Like Immunoreactivity in the Brain and Peripheral Region of Rats. FASEB J., vol. 9, No. 4, Abstract No. 5438, p. A937, 1995.

Snyder et al. HbXL991: A hemoglbin Derivative That is Cross–linked Between the a Subunits is Useful as a Blood Substitute. Proc. Natl. Acad. Sci. USA, vol. 84, pp. 7280–7824, 1987.

Solomon et al. Decrease in Cerebral Blood Flow in Rats After Experimental Subarachnoid Hemorrhage: A New Animal Model. Stroke, vol. 16, No. 1, pp. 58–64, 1985.

Stewart et al. The Role of Endothelium–Derived Relaxing Factor (EDRF) in The Acetylcholine–Induced Dilation of Coronary Resistance Vessels. Pfleugers Arch Eur J. Physiol, vol. 408, Suppl. 1, Abstract No. 81, 1987.

Suzuki et al. Hemoglobin Augmentation of Interleukin–1b–Induced Production of Nitric Oxide in Smooth–Muscle Cells. Journal of Neurosurgery, vol. 81, pp. 895–901, 1994.

Swift et al. Subarachnoid Hemorrhage Fails to Produce Vasculopathy or Chronic Blood Flow Changes in Rats. Stroke, vol. 19, No. 2, pp. 878–882, 1988.

Szabo et al. Uptake and Release of Serotonin in Rat Cerebrovascular Nerves After Subarachnoid Hemorrhage. Stroke, vol. 23, No. 1, pp. 54–61, 1992.

Takayasu et al. A Role of Nitric Oxide in Vasomotor Control of Cerebral Parenchymal Arterioles in Rats. Journal of the Automatic Nervous System, vol. 49, pp. S63–S66, 1994.

Tanishima, Cerebral Vasospasm: Contractile Activity of Hemoglobin in Isolated Canine Basilar Arteries. Journal Neurosurgery, vol. 53, pp. 787–793, 1980.

Toda, Mechanisms of Contracting Action of Oxyhemoglobin in Isolated Monkey and Dog Cerebral Arteries. American Journal of Physiology, vol. 258, pp. H57–H63, 1990.

Toda et al. Constrictor Action of Oxyhemoglobin in Monkey and Dog Basilar Arteries in Vivo and in Vitro. American Journal of Physiology, vol. 260, pp. H420–H425, 1991.

Verlooy et al. The Course of Vasospasm Following Subarchnoid Haemorrhage in Rats. Acta Neurochir (Wien), vol. 117, pp. 48–52, 1992.

Vincent et al. Intracoronary Diaspirin Crosslinked Hemoglobin (DCLHb) Infusion During Coronary Balloon Occlusion in Dogs and Pigs. J. Molec. Cell. Cardiol., vol. 23, No. 3 Supplement, p. S8, 1991 (abstract).

Vogel et al. Coronary Constrictor Effect of Stroma–Free Hemoglobin Solutions. American Journal of Physiology, vol. 251, pp. H413–H420, 1986.

Voldby et al. Cerebrovascular Reactivity in Patients with Ruptured Intracranial Aneurysms. Journal Neurosurgery, vol. 62, pp. 59–67, 1985.

Voldby et al. Regional CBF, Intraventricular Pressure, and Cerebral Metabolism in Patients with Ruptured Intracranial Aneurysms. Journal Neurosurgery, vol. 62, pp. 48–58, 1985.

Wallace et al. Mechanism of Autooxidation for Hemoglobins and Myoglobins. The Journal of Biological Chemistry, vol. 257, No. 9, pp. 4966–4978, 1982.

Wellum et al. Cerebral Vasoactivity of Heme Proteins in vitro. J. Neurosurgery, vol. 56, pp. 777–783, 1982.

Wellum et al. Dose Responses of Cerebral Arteries of the Dog, Rabbit, and Man to Human Hemoglobin in vitro. J. Neurosurgery, vol. 53, pp. 486–490, 1980.

Winslow, A Model for Red Cell O2 Uptake. International Journal of Clinical Monitoring and Computing, vol. 2, pp. 81–93, 1985.

Winterbourn, Free–Radical Production and Oxidative Reactions of Hemoglobin. Environmental Health Perspectives, pp. 321–330, 1985.

Wyngaarden et al. Cecil Textbook of Medicine. W. B. Saunders Company, 19th Edition, vol. 2, pp. 2162–2165, 1992.

Yang et al. Experimental Intracerebral Hemorrhage: Relationship Between Brain Edema, Blood Flow, and Blood––Brain Barrier Permeability in Rats. J. Neurosurg., vol. 81, pp. 93–102, 1994.

Yellon et al. Myocardinal Protection: The Pathophysiology of Reperfusion and Reperfusion Injury. Chemical Abstracts, Abstract No. 12626lt, vol. 116, No. 13, p. 640, 1992.

Yonas, Cerebral Blood Flow Assessment Following Subarachnoid Hemorrhage. Biological Abstracts, vol. 47, No. 2, Ref #25361, pp. 59–66, 1994.

Zikria et al. A Biophysical Approach to Capillary Permeability. Surgery, vol.. 105, No. 5, pp. 625–631, 1989.

Zikria et al. Hydroxyethyl Starch Macromolecules Reduce Myocardial Reperfusion Injury. Arch Surgery, vol. 125, pp. 930–934, 1990.

d'Avella et al. Early Blood–Brain Barrier Changes After Experimental Subarachnoid Haemorrhage: A Quantitative and Electon Microscopy Study. Clinical Neurochirurgica, vol. 0, No. 0, pp. 48–51, 1994.

Halstenson et al., "Pharmacological Profile of Diaspirin Cross–linked Hemoglobin (DCLHb) in Hemodialysis (HD) Patients," J. of Am. Soc. Nephrology, vol. 5, No. 3, Abstract No. 84p, p. 451, 1994.

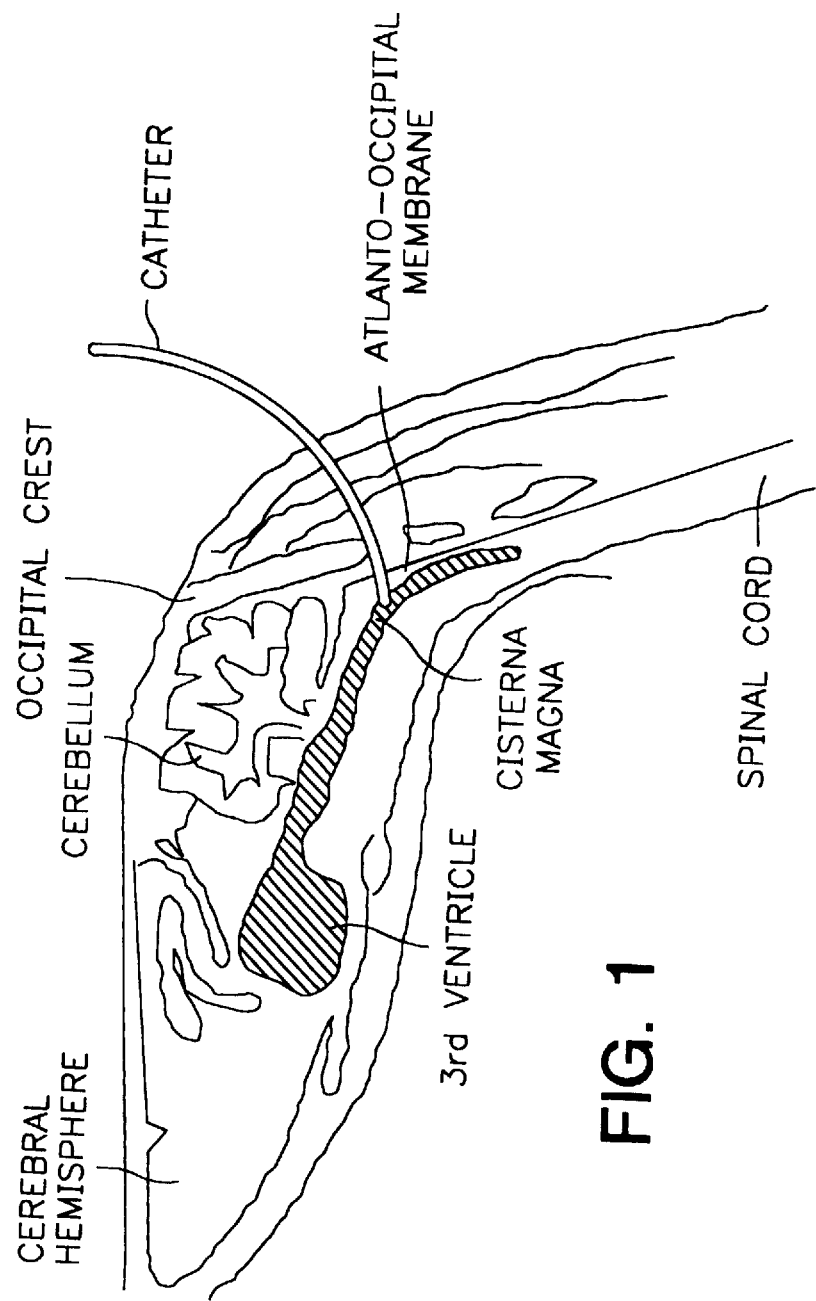

SLICE 1

SLICE 2,3,4

HIPPOCAMPUS CA1/CA3

SLICE 5,6

CEREBELLAR LOBULES

USE OF CROSS-LINKED HEMOGLOBIN IN TREATING SUBARACHNOID HEMORRHAGE

REFERENCE TO RELATED APPLICATIONS

This is a continuation-in-part of application Ser. No. 08/419,209, filed Apr. 10, 1995, now abandoned.

BACKGROUND OF THE INVENTION

A release of blood into the subarachnoid space occurs following breach of a blood vessel, as for example, in the rupture of an aneurysm in the arterial blood supply to the brain. The pooling of blood in the subarachnoid space exposes the brain dura mater to blood contact. Over a period of two to three days a number of events are thought to occur: red blood cells (RBC) begin to lyse, liberating RBC components including free hemoglobin into the surrounding subarachnoid space, and the subsequent progressive conversion of oxyhemoglobin to methemoglobin with the possible production of superoxide anion radicals. Considerable evidence suggests that these RBC components mediate the pathogenesis of cerebral vasospasm, a condition associated with significant morbidity and mortality.

More recently there have been many attempts to identify and isolate the spasmogen contained in the RBC components. Many investigators have identified hemoglobin as the vasoactive agent. For a comprehensive review, see Macdonald & Weir, *Stroke*, 22:971 (1991). number of investigators have contributed significantly to this research including Miyaoka et al., *Neurol. Med. Chir.*, 16:103 (1976), Sonobe et al., *Acta Neurochir.*, 44:97 (1978), and Okamoto, *Ninnon Geka Hokan*, 51:93 (1982). In addition, the effect of hemoglobin in causing vasoconstriction of cerebral arteries is well documented (for example, see Cook et al., *Proc. West Pharmacol. Soc.*, 22:429 (1979).

The prevailing paradigm in the field is that hemoglobin is the biochemical culprit in initiating vasospasm, although the mechanism of action is incompletely understood. See generally, New Trends in Management of Cerebro-Vascular Malformations, Proceedings of the International Conference, Verona, Italy, eds. Pasqualin et al., Springer-Verlag, New York (1994). One theory is that hemoglobin acts by causing release of endothelin, a powerful vasoconstrictor, which in turn may mediate the vasospasm (Costentino et al., *Stroke*, 25:904 (1994). Another theory is that vasoconstriction results when hemoglobin scavenges nitric oxide.

In subarachnoid hemorrhage, an artery bursts (typically an aneurysm) and floods the subarachnoid space to more or less uniformly coat the brain mass. In the period of about three to four days, the presence of blood components may cause regions of vasospasm, or severe vasoconstriction in which the neural tissue becomes ischemic resulting in neuronal injury and death. The effects may be sufficiently severe and cover a large enough portion of the total brain mass to result in serious neurological impairment or death.

Thus, therapies which prevent or minimize ischemia arising in subarachnoid hemorrhage have great benefit. Heretofore, several drug regimens have been proposed for treating vasospasm. For example, intravenous administration of nicardipine or nimodipine have been used with some success. A discussion of available therapeutic approaches is contained in E. C. Haley, "Principles of Pharmaceutical Therapy for Vasospasm Following Subarachnoid Hemorrhage", New Trends in Management of Cerebro-Vascular Malformations, supra, p. 85.

SUMMARY OF THE INVENTION

Investigators and clinicians have sought therapies, generally comprising a regimen of administering a drug or combination of vasoactive drugs, to improve intracranial blood flow in order to prevent or reduce the amount of permanent injury to the brain tissue in the management of subarachnoid hemorrhage. Accordingly, it is an object of the present invention to provide a method for reducing neuronal damage arising from post-hemorrhage vasospasm.

The present invention is directed to a method of reducing neuronal damage in subarachnoid hemorrhage, reducing the area of hypoperfusion after the onset of subarachnoid hemorrhage, reducing or preventing post-hemorrhagic induced vasospasm following an onset of subarachnoid hemorrhage, or treating ischemic stroke before definitive diagnosis thereof. The method includes administering a therapeutically effective amount of a hemoglobin preparation to a patient after the onset of subarachnoid hemorrhage.

BRIEF DESCRIPTION OF THE DRAWINGS

FIG. 1 is a schematic of a longitudinal cross-section of the rat cranium showing the anatomical relation of the major structures of the brain to the catheter position for subarachnoid infusion of blood in the experimental model.

FIGS. 2a–e depict in cross-section the tissue slices obtained for histological analysis, derived from typical test animals undergoing experimental subarachnoid hemorrhage.

DETAILED DESCRIPTION OF THE PREFERRED EMBODIMENT

Figure 2B:
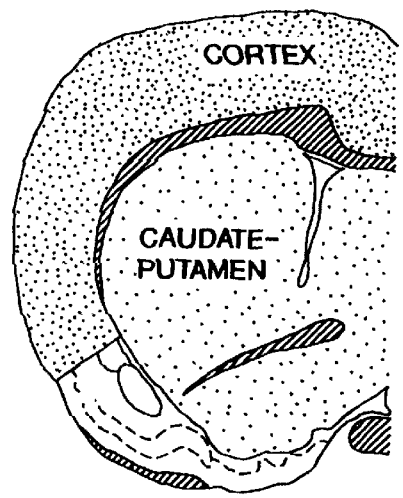

In the present method, hemoglobin solutions are infused into a patient or other mammal after the onset or suspected onset of subarachnoid hemorrhage in a therapeutically effective dose, generally in the range of about 1,000 to about 5,500 milligrams hemoglobin per kilogram of body weight. It is found that contrary to the heretofore observed apparent adverse effects of free hemoglobin in the subarachnoid space, infused hemoglobin reduces the area of hypoperfusion and regions of tissue at ischemic risk, prevents post-hemorrhage vasospasm, and reduces neuronal damage.

Thus, in accordance with the present invention, a method of reducing the area of hypoperfusion and ischemia, preventing or limiting vasospasm, and reducing neuronal damage in patients and other mammals undergoing or suspected of undergoing subarachnoid hemorrhage comprises administering a therapeutically effective amount of a hemoglobin preparation. The dose range is generally about 1,000 to about 5,500 milligrams hemoglobin per kilogram of body weight, and is administered within about 72 hours after the onset of hemorrhage. Administration of hemoglobin up to and during the first 72 hours posthemorrhage may be in a single bolus, or in a series of infusions of individual doses in the about 1,000 to about 5,500 milligrams hemoglobin per kilogram of body weight range.

Administration of a hemoglobin preparation is preferably by intravenous infusion, although arterial cannulization or other drug delivery method may be efficacious. It is apparent that the surprising reduction of tissue ischemia, hypoperfusion, and associated vasospasm results from an action upon the affects tissue beds, so that introduction of the therapeutic hemoglobin at the site of the lesion or directly into the subarachnoid space would not be expected to demonstrate a benefit, and may even precipitate a vasospastic episode. Therefore, a mode of administration involving perfusion of the brain tissue beds, preferably through systemic infusion, is important.

The quantity and timing of hemoglobin administration may vary according to the circumstances of the individual case. The effective dose range is between about 1,000 and about 5,500 milligrams hemoglobin per kilogram of body weight, with a preferred dose of about 2,000 to 4,000 milligrams hemoglobin per kilogram of body weight. It may be advantageous to administer an initial dose of about 1,500 to about 3,000 milligrams hemoglobin per kilogram of body weight with a later supporting dose of a like amount. Since vasospasm may occur over a 3 to 4 day period post-hemorrhage, and because unpolymerized crosslinked hemoglobins have a relatively rapid clearance rate, a multi-dose regimen may be required to maintain hemoglobin concentrations at a therapeutically effective level over a sustained period.

The level of free circulating hemoglobin may be monitored conventionally, and treatment levels may be adjusted for parameters known to those skilled in the art. It is also advantageous to administer equivalent doses of hemoglobin in situations where ischemic stroke is suspected from hemorrhagic or thrombolitic origins, and before definitive diagnosis has been obtained.

As used herein, the term "hemoglobin" includes all oxygen-carrying proteins containing globin or globin-like polypeptides and heme, and being capable of transporting and releasing oxygen to cells, tissues or organs when introduced into the blood stream of a mammal in a physiologically compatible carrier. The term "hemoglobin" includes all naturally- and non-naturally-occurring hemoglobin. The term "hemoglobin preparation" includes hemoglobin in a physiologically compatible carrier or lyophilized hemoglobin reconstituted with a physiologically compatible carrier, but does not include whole blood, red blood cells or packed red blood cells.

Naturally-occurring hemoglobin includes any hemoglobin identical to hemoglobin naturally existing within a cell. Naturally-occurring hemoglobin is predominantly wild-type hemoglobin, but also includes naturally-occurring mutant hemoglobin. Wild-type hemoglobin is hemoglobin most commonly found within natural cells. Wild-type human hemoglobin includes hemoglobin A, the normal adult human hemoglobin having two α and two β-globin chains. Mutant hemoglobin has an amino-acid sequence that differs from the amino-acid sequence of wild-type hemoglobin as a result of a mutation, such as a substitution, addition or deletion of at least one amino acid. Adult human mutant hemoglobin has an amino-acid sequence that differs from the amino-acid sequence of hemoglobin A. Naturally-occurring mutant hemoglobin has an amino-acid sequence that has not been modified by humans. The naturally-occurring hemoglobin of the present invention is not limited by the methods by which it is produced. Such methods typically include, for example, erythrocytolysis and purification, recombinant production, and protein synthesis.

Non-naturally-occurring hemoglobin includes mutant hemoglobin having an amino-acid sequence different from the amino-acid sequence of hemoglobin naturally existing within a cell, and chemically-modified hemoglobin. Such non-naturally-occurring mutant hemoglobin is not limited by its method of preparation, but is typically produced using one or more of several techniques known in the art, including, for example, recombinant DNA technology, transgenic DNA technology, protein synthesis, and other mutation-inducing methods.

Chemically-modified hemoglobin is a natural or nonnatural hemoglobin molecule which is bonded to or encapsulated by another chemical moiety. For example, a hemoglobin molecule can be bonded to pyridoxal-5'-phosphate, or other oxygen-affinity-modifying moiety to change the oxygen-binding characteristics of the hemoglobin molecule, to crosslinking agents to form crosslinked or polymerized hemoglobin, or to conjugating agents to form conjugated hemoglobin. Conjugated, polymerized and crosslinked hemoglobins generally exhibit longer intravascular retention times than unmodified hemoglobin.

Several examples of hemoglobin modification technology which can be used in the practice of the present invention have been described in the scientific literature (reviewed by R. M. Winslow (1992) in Hemoglobin-Based Red Cell Substitutes, The Johns Hopkins University Press, Baltimore, Md.). Some representative methods of preparing chemically-modified hemoglobin for use in the invention are described below.

Hemoglobin can be modified to improve its oxygen-binding affinity. Reagents that bind to the 2,3-diphosphoglycerate binding site of a hemoglobin molecule, reduce the oxygen affinity of the hemoglobin molecule, and prolong intravascular retention are described in U.S. Pat. Nos. 4,529,719 and 5,380,824 (pyridoxal-5'-phosphate), U.S. Pat. No. 4,600,531 (carboxyl-, phosphonate-, phosphate-, sulfonate- or sulfate-phenyl ester-containing compounds such as mono(3,5-dibromosalicyl)fumarate), U.S. Pat. No. 5,268,500 (arylureido acid compound), U.S. Pat. No. 5,382,680 (2[4-(((benzyl)amino)carbonyl) phenoxy]-2-methyl propionic acids), and U.S. Pat. Nos. 5,290,803 and 5,432,191. In general, any method of preparing or modifying hemoglobin such that the hemoglobin can transport and release oxygen is suitable in the present method. Preferably, the hemoglobin has a $P_{50}$ of between about 20 and about 45 mm Hg.

An encapsulated hemoglobin is hemoglobin surrounded by a material which retains the hemoglobin within the material yet allows smaller molecules to pass through the material to react with hemoglobin and reaction products to pass out of the material. Materials for encapsulating hemoglobin are described in U.S. Pat. No. 4,343,715 (polyurethane, acrylic gels, maleic anhydride polymers, epoxy polymers, glutaronic aldehyde polymers), U.S. Pat. Nos. 5,061,688, 5,217,648 and 5,438,041 (oil emulsion), and U.S. Pat. Nos. 4,322,311, 4,324,683 and 4,390,521 (polymers).

A conjugated hemoglobin is at least one non-hemoglobin molecule covalently or ionically bound to a hemoglobin. In some embodiments, the non-hemoglobin molecule can also form an intermolecular crosslink between hemoglobin molecules. Conjugating materials and methods for preparing hemoglobin conjugates are described in WO 91/07190 (polyalkylene glycol), U.S. Pat. Nos. 4,670,417, 5,091,176, 5,219,564, 5,234,903, 5,312,808 and 5,386,014, WO 94/04193, WO 94/09027 and Japanese Patent Nos. 59-104323 and 61-053223 (polyalkylene oxide), U.S. Pat. Nos. 5,349,001 and 5,405,877 (cyclic imide thione activated polyalkylene oxide), U.S. Pat. No. 4,301,144 (polyalkylene glycol, alkylene glycol copolymers, alcohol-polyalkylene glycol ether copolymers, carboxylic acid-polyalkylene glycol ester copolymers, and amine-polyalkylene glycol derivatives), U.S. Pat. Nos. 4,267,234, 4,267,435 and 4,369, 226 (polyglutaraldehyde), Canadian Patent Application No. 2,074,852 (divinyl sulfone), U.S. Pat. No. 4,412,989 (polyether), U.S. Pat. No. 4,377,512 (inulin), U.S. Pat. Nos. 5,079,337 and 5,110,909 (polysaccharide, polyvinyl alcohol, polyvinyl pyrrolidone, polymethacrylate, polypeptide, polyalkylene glycol, hydroxyalkyl starch, and dextran), U.S. Pat. No. 4,920,194 (sulfated glycosaminoglycan fragments, such as heparin), U.S. Pat. No. 4,970,156 (active protein), U.S. Pat. No. 4,336,248 (dialdehyde), U.S. Pat. No. 4,900,780 (hydroxyethyl starch or tetronic polymer), and U.S. Pat. Nos. 4,698,387, 4,935,465, and 5,514,780.

Crosslinked hemoglobin is intramolecularly linked between globin or globin-like protein subunits by a crosslinking agent. A subunit is one globin or globin-like protein of a hemoglobin molecule. Intramolecular crosslinking prevents dissociation of globin or globin-like proteins when hemoglobin is administered in vivo. Hemoglobin A, for example, can dissociate into two α-β globin dimers if the dimers are not crosslinked. Crosslinked hemoglobins and methods for their preparation are described in U.S. Pat. Nos. 4,529,719 and 4,600,531 (α—α linkage using diphenyl ester derivatives such as bis(3,5-dibromosalicyl)fumarate), U.S. Pat. Nos. 4,001,401 and 4,053,590 (α-β globin linkage using halogenated cycloalkanes, diepoxides, and diazobenzidines), U.S. Pat. No. 4,857,636 (aldehyde derived from oligosaccharide), U.S. Pat. No. 5,334,705 (benzenetricarboxylate), WO 94/21682 (β—β globin linkage using di- or trisaccharide), U.S. Pat. Nos. 5,290,919 and 5,387,672 (di- or trivalent compounds), U.S. Pat. No. 5,334,707 (β—β or α—α linkage using acyl phosphate ester), U.S. Pat. Nos. 5,362,885 and WO 92/09630 (imidoesters, such as dimethyl adipimidate or dimethyl suberimidate), U.S. Pat. No. 5,514,780 (polycarboxylic acid), U.S. Pat. No. 5,399,671 and WO 90/13309 (β—β linkage), and U.S. Pat. No. 4,473,496 (dialdehyde).

A polymerized hemoglobin is intermolecularly linked between hemoglobin molecules. Polymerization generally increases the molecular weight of the hemoglobin, which improves its intravascular half-life. Polymerization agents for preparing polymerized hemoglobin are described in pending U.S. applications Ser. Nos. 08/149,679, 08/173,882, 08/480,593, and 08/473,459, U.S. Pat. No. 4,777,244 (aliphatic dialdehyde), U.S. Pat. No. 5,349,054 (benzenepentacarboxylate), WO 94/14460 (transglutaminase), and EP 201618 (glutaraldehyde).

Hemoglobins can also be modified by a combination of the methods described above, for example, as described in Japanese Patent Nos. 59-089629, 59-103322, and 59-104323 (pyridoxal-5'-phosphate modification and polyethylene glycol conjugation of hemoglobin), U.S. Pat. No. 5,248,766 (crosslinking and polymerization of tetrameric hemoglobins with oxiranes), U.S. Pat. Nos. 4,650,786, 4,710,488 and 4,900,816 (inositol phosphate aldehyde modification and polysaccharide conjugation of hemoglobin), U.S. Pat. Nos. 5,189,146 and 5,364,932 (di- or polyaldehydes for intra- and intermolecular crosslinking), EP 361719 (pyridoxylation, dicarboxylic acid halo-ester crosslinking, and polymerization), WO 90/13309 (pyridoxal-5-phosphate derivative for intramolecular crosslinking and glutaraldehyde for polymerization), U.S. Pat. No. 5,439,882 (periodate-oxidized ATP intramolecular crosslinking and periodate-oxidized adenosine polymerization), U.S. Pat. Nos. 4,826,811 and 5,194,590 (pyridoxylation and glutaraldehyde polymerization), and U.S. Pat. No. 4,529,719 (intramolecularly crosslinked with diaspirin ester and pyridoxylated).

Recombinantly-produced hemoglobin is produced by recombinant DNA methodologies, for example, by site-directed mutagenesis, gene fusion, or transfecting a genetically engineered plasmid into a microorganism such as a bacterium or yeast, a cultured cell such as an insect cell, a mammalian cell, or plant cell, a transgenic plant, a transgenic animal, or any other host cell or organism, where the plasmid includes a nucleic acid polymer (e.g., cDNA) which encodes a globin protein, a fusion protein, or a protein similar to globin that can reversibly bind oxygen. Recombinant mutant and artificial hemoglobins and their production in cell cultures or fluids is described in U.S. Pat. Nos. 5,449,759 and 5,028,588, and in WO 88/09179, AU 614525, GB 2234749 B, and EP 358708 B1. Di-α and di-β globin-like polypeptides and other hemoglobin variants produced in bacteria and yeast, and other fused hemoglobins, are described in WO 90/13645, WO 91/16349, EP 561245 A1, and AU 614525. Non-natural multimeric hemoglobin-like proteins are described in WO 93/09143. Production and recovery of human hemoglobin from transgenic pigs are described in WO 92/22646, WO 93/25071, and WO 95/04744. Methods for the preparation and purification of hemoglobin derived from erythrocyte and non-erythrocyte cells are described in WO 92/22646, WO 93/25071, WO 95/04744, WO 95/14038, and WO 96/15151.

Hemoglobins useful in the methods of the present invention are also free of pyrogens, toxins and other contaminants. Pyrogen-free hemoglobin is hemoglobin that is absolutely free of fever-producing contaminants, or hemoglobin that contains amounts of fever-producing contaminants that are physiologically acceptable to a patient to which the hemoglobin will be administered. Bacterial endotoxins contaminate hemoglobin derived from erythrocytes. The endotoxins are released when erythrocytes are disrupted to obtain hemoglobin. Recombinant hemoglobin produced in non-erythrocyte host cells such as bacteria can also become contaminated with cellular components such as proteins, toxins, or polysaccharides that can elicit toxic or pyrogenic responses when administered to mammals (Rietschel et al. (1992) *Scientific American* 267:54–61; Suffredini et al. (1989) *New Eng. J. Med.* 321:280–287).

Hemoglobins for use in the present invention are also stroma-free. Stroma, the insoluble cell membrane fragments that contaminate hemoglobin derived from lysed erythrocytes, is toxic and has been reported to cause dyspnea, bronchospasm, hypotension, arrhythmia, disseminated intravascular coagulation, activation of complement, and renal, myocardial, and hepatic changes associated with ischemia and acute inflammation (Feola (1988) *Surgery, Gynecology & Obstetrics* 166:211–222; MacDonald et al. (1988) F.A.S.E.B. J. 2(6) Abstr. 8217; Stone et al. (1979) *Surgery, Gynecology & Obstetrics* 149:874–876; Rabiner et al. (1967) *J. Exp. Med.* 126:1127–1142. For purposes of the present invention, "stroma-free hemoglobin" is hemoglobin, as defined herein, which is either absolutely free of stroma, or which contains stroma at concentrations that are physiologically acceptable (i.e., do not cause adverse side effects) in a patient. Stroma-free hemoglobin that is absolutely free of stroma includes recombinant hemoglobin produced in a non-erythrocyte. Stroma-free hemoglobin that contains stroma at physiologically acceptable levels includes, for example, purified hemoglobin derived from erythrocytes.

The hemoglobin can be dialyzed or exchanged by ultrafiltration into a physiologically acceptable solution preferably to between about 1 and about 20 g/dl hemoglobin. The solution generally comprises a physiologically compatible electrolyte vehicle isosmotic with whole blood and which maintains the reversible oxygen-carrying and delivery properties of the hemoglobin. The physiologically acceptable solution can be, for example, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates. Such solutions can be administered parenterally, for example by intravenous or intraarterial injection or infusion, without adverse side effects. The hemoglobin can also be lyophilized for storage and reconstituted prior to use. Methods for preparing such solutions or lyophilized powders are known in the art.

A preferred hemoglobin for use in the present method is hemoglobin crosslinked with bis(3,5-dibromosalicyl)-fumarate to create a fumarate crosslink between the two α subunits (DCLHb™, manufactured by Baxter Healthcare, Deerfield, Ill.). This crosslinked hemoglobin is more fully described, together with methods for its preparation, in U.S. Pat. Nos. 4,598,064, 4,600,531, and RE 34,271, omitting the chromatography step. This hemoglobin is preferably manufactured under the conditions disclosed in U.S. Pat. Nos. 4,831,012, 4,861,867, 5,128,452 and 5,281,579 and U.S. patent application Ser. No. 07/207,346.

In practice, a preferred DCLHb™ solution, manufactured by Baxter Healthcare Corporation and useful in the present invention, contains 10 g/dl of modified tetrameric hemoglobin in a balanced electrolyte solution. The product is prepared from units of human red cells from volunteer donors which have been tested and found negative for HbsAg, HIV-1 and 2, and HCV. During manufacture, the red cells are osmotically lysed to release hemoglobin. After ultrafiltration, the stroma-free hemoglobin is reacted with the diaspirin crosslinking agent to produce a stabilized tetrameric hemoglobin having a fumaryl moiety linking the two α subunits. After crosslinking, the reaction mixture is heated to effect viral deactivation and precipitate extraneous proteins. The precipitate is removed by filtration. The DCLHb™ is then concentrated and diafiltered into a physiologic electrolyte vehicle. The resulting solution is isosmotic with whole blood, hyperoncotic (approximately 40 torr), and has the composition shown in Table 1.

TABLE 1

Chemical Assay of 10% Diaspirin Crosslinked Hemoglobin Solution

| | |
|---|---|
| Hemoglobin content | 10 g/dl |
| Oncotic pressure | 43 mm Hg |
| Osmolarity | 290 mOsm/L |
| pH | 7.4 @ 37° C. |
| $Na^+$ | 145 mEq/L |
| $K^+$ | 4 mEq/L |
| $Ca^{++}$ | 2.3 mEq/L |
| $Mg^{++}$ | 0.9 mEq/L |
| $Cl^-$ | 115 mEq/L |
| Lactate | 34 mEq/L |

Further advantages of present invention will be apparent from the Example which follows.

EXAMPLE

In the following experiments, the effect of a preferred crosslinked hemoglobin, alpha-alpha diaspirin crosslinked hemoglobin (DCLHb), on cerebral blood flow and brain injury was assessed, following experimentally induced subarachnoid hemorrhage in rats. The DCLHb solution, obtained from Baxter Healthcare Corporation (Deerfield, Ill.) was prepared according to Chateerjee et al., *J. Biol. Chem.* 261:9929 (1986).

Outdated human red blood cells were lysed by exposure to hypertonic buffer. The hemolysate was centrifuged to separate and remove stroma lipids. After ultrafiltration, molecular hemoglobin was crosslinked at the α chain by reaction with the diaspirin compound, bis(3,5-dibromosalicyl)fumarate. Elimination of viral contamination and protein purification was achieved by heat pasteurization. Estep et al., "Virus inactivation in hemoglobin solutions by heat", *Blood Substitutes,* Edited by Change TMS, Geyer RP, New York, Marcel Dekker, pp. 129–134 (1989). The final DCLHb solution had a concentration of 10.2 g/dl (see Table 2). The DCLHb solution was stored at −70° C. until needed for the current study at which time it was thawed to 5° C., and on the day of the study passively warmed to room temperature. Oxygen transport of DCLHb is similar to whole blood with a slight right shift in the oxygen dissociation curve. The α—α crosslinking with bis(3,5-dibromosalicyl)fumarate prolongs the intravascular half-life to about 24 hours. The viscosity of DCLHb (1.3 centistokes) is comparable to serum albumin and considerably less than whole blood (>4.0 centistokes).

TABLE 2

Chemical Assay of 10% Diaspirin Crosslinked Hemoglobin Solution

| | |
|---|---|
| Hemoglobin content | 10.2 g/dl |
| Methemoglobin | 0.7 g/dl |
| $P_{50}$ (37° C.) | 32.0 mmHg |
| Osmolality | 290 mOsm/kg |
| Oncotic Pressure | 42.7 mmHg |
| Viscosity | 1.3 centistokes |
| pH | 7.50 |
| $Na^+$ | 140 mEq/L |
| $K^+$ | 5.0 mEq/L |
| $Ca^{++}$ | 2.2 mEq/L |
| $Mg^{++}$ | 1.0 mEq/L |
| $Cl^-$ | 115 mEq/L |
| Lactate | 30 mEq/L |

The subarachnoid catheter was prepared by tying a small knot at one end of a 3 cm length of polyethylene tubing (PE-10). The catheter was trimmed to allow 5 mm between the knot and the proximal end of the catheter. A small amount of cyanoacrylate glue was placed on the knot. The catheter was flushed with saline to assure free passage of fluid and sealed with HematoSeal at the distal end.

Male Spontaneously Hypertensive Rats (weight, 350400 grams; age, 16–20 weeks) were anesthetized with 1.2 MAC isoflurane (1.44% end-tidal) via a face mask as described in Cole et al., *Lab Anim. Sci.,* 40:506 (1990). The animals were placed prone on a stereotaxic head holder. Temperature was servo-controlled at 37° C. The model for experimental subarachnoid hemorrhage has previously been described by Solomon et al., "Decrease in cerebral blood flow in rats after experimental subarachnoid hemorrhage: a new animal model", *Stroke,* 16:58–64. After a betadine prep, the occipital crest was located and a small midline incision made. The occipital bone was cleared of muscular tissue and the atlanto-occipital membrane identified and cleaned of extraneous connective tissue. Hemostasis was achieved with gelfoam as needed. Careful dissection prevented opening of the atlanto-occipital membrane as this lies directly over the cisterna magna and perforation would cause leakage of cerebrospinal fluid (CSF). The catheter was positioned over the membrane and a 22-g needle advanced through the membrane to a depth of <1 mm. A small amount of CSF drainage occurred, confirming correct location, and the catheter was carefully placed in the cisterna magna (see FIG. 1). The cannula was advanced along the inner table of the occipital bone until the knot rested against the membrane (care taken to insure superficial placement). After placement of the catheter a small amount of dental acrylic was applied over the knot to secure it in place. The deep muscle layer was closed and the catheter sutured in place. The superficial muscle layers and skin were closed, and the skin infiltrated with 0.375% bupivicaine. The rat was returned to an incubator and allowed to recover for 72 hours, with a 12 hour light-dark cycle. Rats exhibiting any neurologic sequelae were excluded from further study (rare).

Animal Preparation: Following the 72 hour recovery period, the animals were anesthetized as above, orotracheally intubated and ventilated with a Harvard Rodent Respirator (Boston, Mass.). The femoral vessels were cannulated for continuous blood pressure monitoring (Micro-Med Analyzer, Louisville, Ky.), blood sampling, and fluid administration. Temperature was servo-controlled at 37° C. with a heating blanket. Arterial blood (125 $\mu$l) was collected at 30 minute increments and analyzed for pH, $PaCO_2$, $PaO_2$, glucose, and hematocrit (IL-1306 pH Blood Gas Analyzer, Instrumentation Laboratory, Lexington, Mass.; YSI Model 23-A Glucose Analyzer, Yellow Springs Instruments, Yellow Springs, Ohio; IEC MB Centrifuge Microhematocrit, DAMON/IEC Division, Needham Heights, Mass.). Prior to administration of subarachnoid blood, each rat was placed in a prone, 20° head-down, position to insure entrance of blood into the basal cistern. The sealed catheter was cut at the distal end and 20–50 $\mu$l of CSF aspirated. Fresh autologous blood (0.3 ml) was infused over 10 minutes into the cisterna magna, with an accompanying average increase in mean arterial pressure of 20–30 mmHg for 10 minutes. The rat was maintained in the head-down position for a total of 20 minutes.

Part A: Each rat was randomized to one of the following hypervolemic-hemodilution groups:

Control (n=10): 7.5 ml of fresh donor blood was given (no hematocrit manipulation [45%]).

30/DCLHb (n=10): blood volume and hemocrit (30%) were manipulated by a 3.0 ml exchange transfusion with 10% DCLHb (Baxter Healthcare Corporation, Deerfield, Ill., Lot 94D01AD11) followed by an additional 7.5 ml infusion of DCLHb.

30/Albumin (n=10): blood volume and hematocrit (30%) were manipulated by a 3.0 ml exchange transfusion, and a 7.5 ml infusion, of oncotically-matched (7.5%) human albumin solution (Baxter Hyland, Glendale, Calif., U.S.A.).

Each exchange transfusion was accomplished by simultaneously withdrawing and infusing the appropriate solution at a rate of 1.0 ml/min; and each 7.5 ml hypervolemic infusion was administered over 15 minutes. When given as a bolus, hemoglobin substitutes increase blood pressure. Rabinovici et al., "Characterization of hemodynamic, hematologic, and biochemical responses to administration of liposome-encapsulated hemoglobin in the conscious, freely moving rat", Circ. Shock, 29:115–132 (1989). However, in this species, if DCLHb is given initially as an exchange transfusion, normotension is maintained. Cole et al., "Focal cerebral ischemia in rats: effect of hypervolemic hemodilution with diaspirin crosslinked hemoglobin versus albumin on brain injury and edema", Anesthesiology, 78:335–342 (1993).

The procedure for measuring cerebral blood flow (CBF) is given in Sakurada et al., "Measurement of local cerebral blood flow with iodo-C-14-antipyrine", Am. J. Physiol., 234:H59–H66 (1978) and Cole et al., "Focal cerebral ischemia in rats: effect of hemodilution with $\alpha$—$\alpha$ crosslinked hemoglobin on CBF", J. Cereb. Blood Flow Metab., 12:971–976 (1992). Immediately before CBF determination, physiologic parameters were evaluated as above. 100 $mCikg^{-1}$ of $^{14}C$-iodoantipyrine (New England Nuclear, Boston, Mass.) was given at a constantly increasing rate over 46 seconds. Twenty-one arterial blood samples were collected for determination of $^{14}C$ activity with a quench correction (Beckman 8000 Liquid Scintillation Spectrometer [Beckman, Brea, Calif., U.S.A.]). After the $^{14}C$ was infused, the brains were removed in <60 seconds and placed in 2-methylbutane (−35° C.). The brains were sectioned in 20 $\mu$m increments, and ten sections surrounding each of five anatomically predetermined coronal planes were placed on x-ray film (Kodak OM-1, Rochester, N.Y.) for 21 days. The five anatomical planes were in 2.0 mm sequential increments. Section 1 was at the anterior midline extent of the corpus callosum, and Section 5 was 1.0 mm posterior to the posterior midline extent of the corpus callosum.

After film processing (21 days), assessment of CBF was done with a computer program based on the equation of Sakurada et al., "Measurement of local cerebral blood flow with iodo-C-14-antipyrine", Am. J. Physiol., 234:H59–H66 (1978). A tissue-blood partition coefficient of 0.80 was used, and each autoradiograph calibrated to nine $^{14}C$ standards (Amersham, Arlington Heights, Ill.). By use of a Drexel/DUMAS Image Analysis System (Drexel University, Philadelphia, Pa.) each anatomical section was analyzed to define areas with a CBF of <40 ml-100 $g^{-1}$-$min^{-1}$. All image analysis was performed by an independent observer who was blinded to study protocol. The data was evaluated by analysis of variance with Scheffe's test for multiple comparisons, and mean values compared by t-tests as appropriate. The results are shown in Table 3.

TABLE 3

|  | Control | DCLHb | Alb |
| --- | --- | --- | --- |
| Area of Hypoperfusion (%) | 49 ± 13 | 13 ± 5* | 6 ± 3† |

Table area of hypoperfusion (CBF < 40 ml 100 $g^{-1}$ $min^{-1}$) in a coronal brain section (% of total area, mean ± SD).
*$p < 0.05$ versus the Control group.
†$p < 0.05$ versus the other two groups.

The area of hypoperfusion was less in the DCLHb group versus control, and was less in the Alb group versus the other two groups.

Figure 2A:
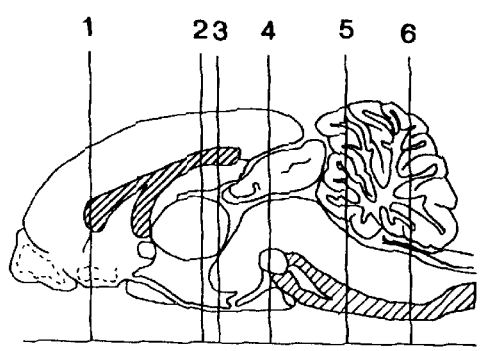
Figure 2C:
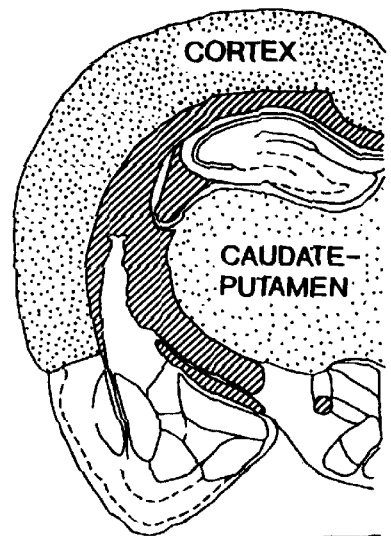
Figure 2D:
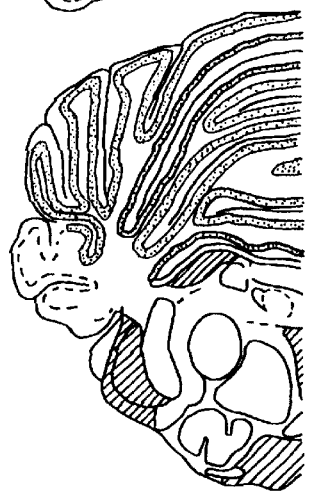

Part B: Different rats were prepared identically to Part A (n=6 for each group). After subarachnoid hemorrhage they were allowed a 96 hour recovery period, after which they were anesthetized, a thoracotomy performed, and the brains perfused with formalin for standard hematoxylin and eosin staining as described in Sheehan et al., "Theory and Practice of Histotechnology", Columbus, Battelee Press (1980). Six coronal sections (7 $\mu$m) coronal sections (from the parietal cortex anteriorly to the cerebellum posteriorly), were evaluated microscopically (X400) for the presence of dead neurons, which were individually counted and reported as a total for each animal (see FIG. 2). Dead neurons were defined as exhibiting pyknosis, karyorrhexis, karyolysis, cytoplasmic eosinophilia or loss of hematoxylin affinity, or dark scalloped and swollen neurons. The criteria described in Garcia et al., "Neuronal necrosis after middle cerebral artery occlusion in Wistar rats progresses at different time intervals in the caudoputamen and the cortex", Stroke, 26:636–643 (1995) were followed.

All microscopy was performed by an independent observer who was blinded to study protocol. The data was evaluated by analysis of variance with Scheffe's test for multiple comparisons, and mean values by t-tests as appropriate. P<0.05 was considered significant. The results are shown in Table 4.

TABLE 4

|  | Control | DCLHb | Alb |
|---|---|---|---|
| Dead Neurons | 510 ± 203 | 166 ± 42† | 284 ± 67* |

Table number of dead neurons in sixteen brain areas (mean ± SD).
*p < 0.05 versus the Control group.
†p < 0.05 versus the other two groups.

The number of dead neurons was less in the Alb group versus the Control group. Significantly, fewer dead neurons were counted in the DCLHb group than in the other two groups.

What is claimed is:

1. A method of reducing neuronal damage in subarachnoid hemorrhage comprising administering a hypervolemic, therapeutically effective amount of a diaspirin-crosslinked hemoglobin preparation to a mammal after the onset of subarachnoid hemorrhage in the mammal to reduce neuronal damage.

2. The method of claim 1 wherein said therapeutically effective amount is in the range of about 1,000 milligrams hemoglobin per kilogram body weight to about 5,500 milligrams hemoglobin per kilogram body weight.

3. The method of claim 1 wherein said therapeutically effective amount of the hemoglobin preparation contains from about 2,000 milligrams hemoglobin per kilogram body weight to about 4,000 milligrams hemoglobin per kilogram body weight.

4. The method of claim 1 wherein the hemoglobin preparation is administered in two infusions with each infusion containing in the range of about 1,500 milligrams hemoglobin per kilogram body weight to about 3,000 milligrams hemoglobin per kilogram body weight.

5. The method of claim 1 wherein the hemoglobin is administered within about 72 hours after the onset of subarachnoid hemorrhage.

6. The method of claim 1 wherein the hemoglobin is a physiologically acceptable solution for parenteral administration in one bolus or in a series of infusions.

7. The method of claim 6 wherein the solution contains from about 1 g/dl to about 20 g/dl of hemoglobin.

8. The method of claim 1 wherein the hemoglobin exhibits an oxygen binding affinity within a range of $P_{50}$ values between about 20 and about 40 mm Hg.

9. A method of reducing the area of hypoperfusion after the onset of subarachnoid hemorrhage comprising administering a therapeutically effective amount of a diaspirin-crosslinked hemoglobin preparation to a mammal after the onset of subarachnoid hemorrhage in the mammal to reduce the area of hypoperfusion resulting from the subarachnoid hemorrhage.

10. The method of claim 9 wherein said therapeutically effective amount is in the range of about 1,000 milligrams hemoglobin per kilogram body weight to about 5,500 milligrams hemoglobin per kilogram body weight.

11. The method of claim 9 wherein said therapeutically effective amount of the hemoglobin preparation contains from about 2,000 milligrams hemoglobin per kilogram body weight to about 4,000 milligrams hemoglobin per kilogram body weight.

12. The method of claim 9 wherein the hemoglobin preparation is administered in two infusions with each infusion containing in the range of about 1,500 milligrams hemoglobin per kilogram body weight to about 3,000 milligrams hemoglobin per kilogram body weight.

13. The method of claim 9 wherein the hemoglobin is administered within about 72 hours after the onset of subarachnoid hemorrhage.

14. The method of claim 9 wherein the hemoglobin is a physiologically acceptable solution for parenteral administration in one bolus or in a series of infusions.

15. The method of claim 14 wherein the solution contains from about 1 g/dl to about 20 g/dl of hemoglobin.

16. The method of claim 9 wherein the hemoglobin exhibits an oxygen binding affinity within a range of $P_{50}$ values between about 20 and about 40 mm Hg.

17. A method of reducing or preventing post-hemorrhagic induced vasospasm following an onset of subarachnoid hemorrhage comprising systemically administering a therapeutically effective amount of a crosslinked, conjugated, encapsulated, recombinant, or polymerized, stroma-free hemoglobin preparation to a mammal after the onset of subarachnoid hemorrhage in the mammal.

18. The method of claim 17 wherein said therapeutically effective amount is in the range of about 1,000 milligrams hemoglobin per kilogram body weight to about 5,500 milligrams hemoglobin per kilogram body weight.

19. The method of claim 17 wherein said therapeutically effective amount of the hemoglobin preparation contains from about 2,000 milligrams hemoglobin per kilogram body weight to about 4,000 milligrams hemoglobin per kilogram body weight.

20. The method of claim 17 wherein the hemoglobin preparation is administered in two infusions with each infusion containing in the range of about 1,500 milligrams hemoglobin per kilogram body weight to about 3,000 milligrams hemoglobin per kilogram body weight.

21. The method of claim 17 wherein the hemoglobin is administered within about 72 hours after the onset of subarachnoid hemorrhage.

22. The method of claim 17 wherein the hemoglobin is a physiologically acceptable solution for parenteral administration in one bolus or in a series of infusions.

23. The method of claim 22 wherein the solution contains from about 1 g/dl to about 20 g/dl of hemoglobin.

24. The method of claim 17 wherein the hemoglobin preparation contains hemoglobin that has been chemically modified to prevent intramolecular dissociation or to increase intravascular persistence.

25. The method of claim 17 wherein the hemoglobin exhibits an oxygen binding affinity within a range of $P_{50}$ values between about 20 and about 40 mm Hg.

26. A method of reducing or preventing post-hemorrhagic induced vasospasm following an onset of subarachnoid hemorrhage comprising systemically administering a therapeutically effective amount of a diaspirin-crosslinked hemoglobin preparation to a mammal after the onset of subarachnoid hemorrhage in the mammal.

27. A method of treating ischemic stroke before definitive diagnosis thereof comprising administering a hypervolemic, therapeutically effective amount of a diaspirin-crosslinked hemoglobin preparation to a mammal after onset of subarachnoid hemorrhage to reduce ischemic area and neuronal damage.

28. The method of claim 27 wherein said therapeutically effective amount is in the range of about 1,000 milligrams hemoglobin per kilogram body weight to about 5,500 milligrams hemoglobin per kilogram body weight.

29. The method of claim 27 wherein said therapeutically effective amount of the hemoglobin preparation contains from about 2,000 milligrams hemoglobin per kilogram body weight to about 4,000 milligrams hemoglobin per kilogram body weight.

30. The method of claim 27 wherein the hemoglobin preparation is administered in two infusions with each infusion containing in the range of about 1,500 milligrams hemoglobin per kilogram body weight to about 3,000 milligrams hemoglobin per kilogram body weight.

31. The method of claim 27 wherein the hemoglobin is administered within about 72 hours after the onset of subarachnoid hemorrhage.

32. The method of claim 27 wherein the hemoglobin is a physiologically acceptable solution for parenteral administration in one bolus or in a series of infusions.

33. The method of claim 32 wherein the solution contains from about 1 g/dl to about 20 g/dl of hemoglobin.

34. The method of claim 27 wherein the hemoglobin exhibits an oxygen binding affinity within a range of $P_{50}$ values between about 20 and about 40 mm Hg.

35. A method of reducing or preventing post-hemorrhagic induced vasospasm following an onset of subarachnoid hemorrhage comprising administering a therapeutically effective amount of crosslinked, stroma-free hemoglobin to a mammal after the onset of subarachnoid hemorrhage in the mammal.

36. The method of claim 35 wherein said therapeutically effective amount contains from about 2,000 milligrams hemoglobin per kilogram body weight to about 4,000 milligrams hemoglobin per kilogram body weight.

37. The method of claim 35 wherein the hemoglobin is administered in two infusions with each infusion containing in the range of about 1,500 milligrams hemoglobin per kilogram body weight to about 3,000 milligrams hemoglobin per kilogram body weight.

38. The method of claim 35 wherein the hemoglobin is administered within about 72 hours after the onset of subarachnoid hemorrhage.

39. The method of claim 35 wherein the hemoglobin is a physiologically acceptable solution for parenteral administration in one bolus or in a series of infusions.

40. The method of claim 39 wherein the solution contains from about 1 g/dl to about 20 g/dl of hemoglobin.

41. The method of claim 35 wherein the crosslinked, stroma-free hemoglobin is diaspirin-crosslinked hemoglobin.

42. (new) The method of claim 35 wherein the hemoglobin exhibits an oxygen binding affinity within a range of $P_{50}$ values between about 20 and about 40 mm Hg.

* * * * *